United States Patent
Freudenberg

(10) Patent No.: US 12,221,620 B2
(45) Date of Patent: Feb. 11, 2025

(54) BIOACTIVE COATING MATERIAL

(71) Applicant: ZetaSCIENCE GmbH, Dresden (DE)

(72) Inventor: Uwe Freudenberg, Dresden (DE)

(73) Assignee: Zeta SCIENCE GmbH, Dresden (DE)

( * ) Notice: Subject to any disclaimer, the term of this patent is extended or adjusted under 35 U.S.C. 154(b) by 0 days.

(21) Appl. No.: 15/182,929

(22) Filed: Jun. 15, 2016

(65) Prior Publication Data

US 2016/0369230 A1  Dec. 22, 2016

(30) Foreign Application Priority Data

Jun. 16, 2015  (DE) .................... 10 2015 109 599.8

(51) Int. Cl.
| | | |
|---|---|---|
| *C09D 189/00* | (2006.01) | |
| *C08J 7/00* | (2006.01) | |
| *C08J 7/04* | (2020.01) | |
| *C08J 7/043* | (2020.01) | |
| *C12M 1/00* | (2006.01) | |
| *C12N 5/00* | (2006.01) | |
| *C12N 11/06* | (2006.01) | |
| *C12N 11/082* | (2020.01) | |
| *C12N 11/087* | (2020.01) | |

(52) U.S. Cl.
CPC .......... *C12N 5/0068* (2013.01); *C08J 7/0427* (2020.01); *C08J 7/043* (2020.01); *C09D 189/00* (2013.01); *C12M 23/20* (2013.01); *C12N 11/06* (2013.01); *C12N 11/082* (2020.01); *C12N 11/087* (2020.01); *C08J 2325/06* (2013.01); *C08J 2489/00* (2013.01); *C12N 2533/20* (2013.01); *C12N 2533/30* (2013.01); *C12N 2533/50* (2013.01); *C12N 2539/00* (2013.01)

(58) Field of Classification Search
None
See application file for complete search history.

(56) References Cited

U.S. PATENT DOCUMENTS

| | | | | |
|---|---|---|---|---|
| 2010/0304427 | A1* | 12/2010 | Faris | C12N 5/0068 435/29 |
| 2012/0034433 | A1* | 2/2012 | George | C08L 25/06 428/195.1 |
| 2015/0010999 | A1* | 1/2015 | Caracci | C12N 5/0037 435/366 |
| 2015/0246132 | A1 | 9/2015 | Wieduwild et al. | |

OTHER PUBLICATIONS

Speight, "Chap. 7: Chemical Transformations in the Environment," in: Environmental Organic Chemistry for Engineers, Elsevier, Inc., pp. 327-330 (2017) (Year: 2017).*
Pagac et al., Langmuir 13:2993-3001 (1997) (Year: 1997).*
Zhao et al., Prog. Polym. Sci. 25:677-710 (2000) (Year: 2000).*
Hershkovits et al., Macromolecules 41:3190-3198 (2008) (Year: 2008).*
Arisaka et al., Macromol. Biosci. 19:6 pages (2019) (Year: 2019).*
Yoo, H.Y. et al. "Recombinant Mussel Coating Protein Fused with Cell Adhesion Recognition Motif Enhanced Cell Proliferation", Biotechnology and Bioprocess Engineering 20, p. 211-217, 2015.

* cited by examiner

*Primary Examiner* — Thea D' Ambrosio
(74) *Attorney, Agent, or Firm* — MARSHALL, GERSTEIN & BORUN LLP

(57) ABSTRACT

The present invention refers to a bioactive coating material for coating plastic materials for cell cultures, comprising a polymer conjugate of each a polymer anchor molecule having surface active anchoring groups and one or more biologically active molecules. The anchor molecule is an amphiphilic molecule with a hydrophobic moiety of styrene-, methacrylic acid-, isobutene-, acrylic acid-, acrylic acid ester-, or methacrylic acid ester units and a hydrophilic moiety of units including carboxyl-, amino-, epoxide-, thiol-, alkine- or azide groups. By selecting cell instructive coating materials cell destiny choices are individually and effectively controllable, in particular, the cell adhesion of almost any cell culture one-way articles by the user. With this concept, new options open up for high-throughput-diagnostics, stem cell-biotechnology and regenerative therapies.

18 Claims, 5 Drawing Sheets

Specification includes a Sequence Listing.

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial sequence
<220> FEATURE:
<223> OTHER INFORMATION: enzymatically cleavable sequence

<400> SEQUENCE: 1

Gly Pro Gln Gly Ile Trp Gly Gln
1               5

<210> SEQ ID NO 2
<211> LENGTH: 5
<212> TYPE: PRT
<213> ORGANISM: Artificial sequence
<220> FEATURE:
<223> OTHER INFORMATION: Amino acid sequence of an adhesion peptide

<400> SEQUENCE: 2

Arg Gly Asp Ser Pro
1               5

<210> SEQ ID NO 3
<211> LENGTH: 6
<212> TYPE: PRT
<213> ORGANISM: Artificial sequence
<220> FEATURE:
<223> OTHER INFORMATION: Amino acid sequence of an adhesion peptide

<400> SEQUENCE: 3

Ser Ile Lys Val Ala Val
1               5

<210> SEQ ID NO 4
<211> LENGTH: 5
```

```
<212> TYPE: PRT
<213> ORGANISM: Artificial sequence
<220> FEATURE:
<223> OTHER INFORMATION: Amino acid sequence of an adhesion peptide

<400> SEQUENCE: 4

Tyr Ile Gly Ser Arg
1               5

<210> SEQ ID NO 5
<211> LENGTH: 7
<212> TYPE: PRT
<213> ORGANISM: Artificial sequence
<220> FEATURE:
<223> OTHER INFORMATION: Amino acid sequence of an adhesion peptide

<400> SEQUENCE: 5

Glu Ile Asp Gly Glu Leu Thr
1               5

<210> SEQ ID NO 6
<211> LENGTH: 7
<212> TYPE: PRT
<213> ORGANISM: Artificial sequence
<220> FEATURE:
<223> OTHER INFORMATION: Amino acid sequence of an adhesion peptide

<400> SEQUENCE: 6

Glu Ile Lys Leu Leu Ile Ser
1               5

<210> SEQ ID NO 7
<211> LENGTH: 12
<212> TYPE: PRT
<213> ORGANISM: Artificial sequence
<220> FEATURE:
<223> OTHER INFORMATION: Amino acid sequence of an adhesion peptide

<400> SEQUENCE: 7

Arg Lys Arg Leu Gln Val Gln Leu Ser Ile Arg Thr
1               5                   10

<210> SEQ ID NO 8
<211> LENGTH: 8
<212> TYPE: PRT
<213> ORGANISM: Artificial sequence
<220> FEATURE:
<223> OTHER INFORMATION: Amino acid sequence of an adhesion peptide

<400> SEQUENCE: 8

Cys Trp Gly Arg Gly Asp Ser Pro
1               5
```

BIOACTIVE COATING MATERIAL

CROSS-REFERENCES TO RELATED APPLICATIONS

This application claims the priority of German Patent Application, Serial No. 10 2015 109 599.8, filed Jun. 16, 2015 pursuant to 35 U.S.C. 119(a)-(d) the description of which is hereby incorporated by reference.

BACKGROUND OF THE INVENTION

The invention refers to a bioactive coating material for coating of plastic materials for cell cultures, preferably plastic one-way materials, for example, polystyrene (TCP) as plastic. In particular, the invention refers hereby to a cell instructive coating material for cell culture materials of plastic, for example, polystyrene. The invention opens new possibilities for in situ coatings in research and biotechnology.

Currently, cell culture applications in the area of research, biotechnology and medicine requires use of masses of plastic one-way articles. In the majority of applications there is cell contact with the material surface, a so-called adherent cell culture. Cell instructive in this context means a signal which influences the cell adhesion and cell fate decisions such as migration, proliferation and differentiation of the cells.

Cell culture one-way products are used in ever rising numbers in important technology fields. In 2009, a global market volume for cell culture plates was in the area of $500 million US with economic focus in USA, Europe and Japan, wherein due to dynamic growth rates in the biotechnology and life science sectors yearly growth rates were discussed of 100% up to 2015. Cell culture plates are currently based on so-called tissue culture plastic (TCP), that is, polystyrene-(PS)-materials that are functionalized for improved cell instructive surface properties, especially for the stimulation of cell adhesion. Recently, two different concepts were predominantly applied: (I) chemical surface modification and (II) coatings with isolated proteins of the extracellular matrix from native sources (ECM).

The first group (I) includes those on the EU or global market established plasma functionalized TCP products for improvement of wetting and also covalent or physisorptive coupled adhesive coatings. Thus, on the one hand targeted functional groups, for example permanently cationic or anionic charged surfaces, i.e. BD PureCoat amine/carboxyl; BD Bioscience, and other polar groups i.e. Greiner CELL-STAR®, Corning® CELLBIND® are introduced into the material surface, or poly cationic coatings, i.e. Poly-D or Poly-L-Lysine, i.e. Nunclon® BD BioCoat™ and Corning® Poly(D-Lysine) deposited that improve the binding of ECM proteins and thus indirectly improve the cell adhesion and influence further cell fate decisions.

The second group (II) of commercially available coatings are isolated ECM-proteins from biological sources for example, collagen, fibronectin or laminin. Examples of such products are Greiner CELLCOAT®, MilliporeMillicoat™ or BD BioCoat™. In addition, a first application of decellularized extracellular matrices of endothelial cells is known, for example, of the company Novamed Ltd.-Coatings.

The first group (I) of functionalization concepts serves to improve the adherence of cell secreted proteins and other matrix constituents at the plastic surfaces and thus can contribute indirectly the promotion of cell adhesion and the control of cell fate decisions. An advantage of these coatings is that the product does not contain biological components, so that the properties are easy to control and the products are easy to sterilize and to store.

The second group (II) utilizes isolated proteins from biological sources that contain specific peptide sequences that are bound by cellular receptors and thus control the cell adhesion or further cell fate decisions. The advantage of these preparations is that the cells interact directly with the protein coatings.

Commercially established bioactive coatings are however based increasingly on the use of surface-linked peptide sequences. These are mostly covalently anchored on TCP, for example with CORNING®, Synthemax™ and Biosciences® BioPure™, wherein meanwhile at least one example exists where adhesion peptides can be adsorptively coupled directly at the end user via an anchor of hydrophobic amino acids, as with Advanced Biomatrix PEPTITE 2000®. The advantage of these coatings resides in the utilization of fully synthetic adhesion peptides for mediating cell adhesion, wherein the commercial introduction to divers global market leaders for cell culture articles shows the potential of such bio-adhesive coatings.

With chemical surface modifications for increased bonding of cell secreted proteins, the indirect promotion of cell adhesion hardly permits control over the final strength of the cell adhesion or the kind of modulation of further cell fate decisions. In addition, such functionalizations cannot be carried out by the end user, so that one has to resort to cell culture articles limited in regards to their geometry, offered by the manufacturer.

The printed publication Yoo, H., Y et al., "Recombinant Mussel Coating Protein Fused with Cell Adhesion Recognition Motif Enhanced Cell Proliferation", Biotechnology and Bioprocess Engineering 20, S. 211 to 217, 2015, describes a durable bioactive coating of a biomedical substrate surface of polystyrene (TCP). To realize such a coating, the fusion protein Fp-1-RGD is genetically constructed and produced in *Escherichia coli*. After coating of a TCP cell culture carrier (TCP) with Fp-1-RGD it shows an improved cell proliferation of pre-osteoblasts as compared to uncoated TCP-cell culture carriers.

The disadvantage of coatings with isolated ECM-proteins from native sources, that is, proteins of the extracellular matrix, lies in the coating properties that can only be partially controlled with the possibility that biologically active signaling molecules, such as hormones, neurotransmitters, cytokines, growth factors and chemokines are contaminating the cell culture thereby influencing the parameters to be investigated. Such products are also problematic relative to storage and sterility. The last group of bioactive coatings with synthetic adhesion peptides, is limited by the technology dependent variability of functionalization to certain peptide sequences and physico-chemical surface properties which makes a desired gradation of cell adhesion and of other cell fate decisions not possible. It can be assumed that especially in complex cell culture media, a suitable anchoring of peptides cannot be realized, that is, that the peptides together with their hydrophobic anchor molecules are relatively easily displaced from the TCP surface and thus cannot confer sufficient stability for cell adhesion. Besides these disadvantages, there is also the high cost of such coating systems.

SUMMARY OF THE INVENTION

An object of the present invention is to provide a bioactive coating system, in particular a cell instructive coating system. This coating material should not develop any toxicity relative to the cells when applied in normal amounts and should also have a sufficient coating stability when treated with rinsing solvents or complex cell culture media, especially buffer solvents or serum-containing media.

That object is being fulfilled with a bioactive coating material suitable for cell culture carriers of plastic, in particular cell cultureone-way materials, for example, polystyrene (TCP) as plastic. It comprises a polymer conjugate of a polymer anchor with surface active anchor groups on the on hand and with one or more biologically active molecules on the other hand. According to the present invention the anchor molecule is an amphiphilic molecule having a hydrophobic moiety of styrene-, methacrylic acid-, isobutene-, acrylic acid-, acrylic acid ester-, or methacrylic acid ester units and a hydrophilic moiety from carboxyl-amino, epoxide, thio-, alkyne-or azide groups containing units. As monomeric units with amino groups, amino acrylate or amino methacrylate units are especially suitable. Preferably, the anchor molecule is an amphiphilic molecule with a hydrophobic moiety from styrene-, methacrylic acid- or isobutene units and a hydrophilic moiety of maleic acid anhydride or maleic acid units.

As bioactive coating material it is preferred to utilize a cell instructive coating material, in particular, cell adhesive coating material. Compared to that, bioactive coatings materials can be also utilized including molecules that contain anti-adhesive effecting molecules, for example, polyethylene glycol (PEG) which reduce cell adhesion and in this manner act likewise cell instructive. By selecting these coating materials, the user can control cell fate decisions, in particular, cell adhesion, on almost all cell culture articles, especially cell culture one-way articles individually and effectively. This concept opens up valuable new options for high through-put diagnostics, stem cell-biotechnology and regenerative therapies. In an extension of the afore-described prior art, a fully synthetic coating was developed that combines the advantages of the afore-described methods without having to rely on biological sources. As an added advantage, the application of an adhesive coating can be realized directly by the end user as a simple adsorption process from aqueous solutions.

The bioactive coating materials, in addition to cell instructive effecting molecules can also include antimicrobial, that is, biocidal or biostatic effective molecules. Preferred are in particular antibacterial coating materials.

According to one embodiment of the present invention, the biologically active molecule is linked to the anchor molecule by an enzymatically cleavable peptide sequence.

Preferably, the biologically active molecule is hereby bound to the anchor molecule by an enzymatically cleavable peptide sequence which is cleaved, for example, by a class of peptidases, for example, metal-proteases, cysteine-, aspartyl-, serine-, and threonyl-proteases.

According to a further embodiment of the present invention, the biologically active molecule is bound to the anchor molecule by an enzymatically cleavable peptide sequence consisting of 5 to 25 amino acid residues, which for example contains the amino acid sequence GPQGIWGQ-SEQ ID NO. 1.

According to a further embodiment of the present invention, the biologically active molecule is a signal molecule, preferably from the group of neurotransmitters, hormones, cytokines, growth factors or chemokines.

According to a further preferred embodiment of the present invention, the biologically active molecule is a peptide which can influence cell fate decisions. According to an especially preferred embodiment, the biologically active molecule is a peptide unit from a protein derived from an extracellular matrix (ECM) such as for example, collagen, fibronectin or laminin. For example. this can be an adhesion peptide consisting of 3 to 50 amino acid residues. The biologically active molecule, according to an advantageous embodiment, is an adhesion peptide that contains the amino acid sequence RGD or RGDSP-SEQ ID NO. 2 or SIKVAV-SEQ ID NO. 3 or YIGSR-SEQ ID NO. 4 or EIDGELT-SEQ ID NO. 5 or EIKLLIS-SEQ ID NO. 6 or RKRLQVLSIRT-SEQ ID NO.7.

To control the cell fate decisions, especially to confer adhesion, the short peptide units derived from ECM proteins that bind natural cellular receptors are generated through solid phase peptide synthesis. These peptide units are then covalently coupled to the synthetic polymer anchor molecules, that are markedly surface active. These anchor molecules have accordingly a hydrophobic, that is a surface affinity moiety and a hydrophilic, that is, a moiety conferring water solubility, that is, they are amphiphil. This way such molecules can be effectively deposited from aqueous solutions on various plastic surfaces. For example, this can be realized directly by the end user. The possibility to use polymer anchors having differently strong surface affinity, are coupled to various peptide sequences of signal molecules, allows cell fate decisions, especially adhesion of different cell types, to be modulated in a defined and cost efficient manner.

Advantageously, anchor molecules are utilized that exhibit several groups along the polymer chain for reaction with functional groups or signal molecules. In one embodiment the anchor molecule is a molecule of a copolymer with alternating isobutene and maleic acid anhydride units or alternating isobutene- and maleic acid units. Such an anchor molecule preferably has a molar mass of 4,000 g/mol.

In a particularly advantageous embodiment of the present invention, the anchor molecule is a copolymer with alternating styrene-and maleic acid anhydride units or alternating styrene- and maleic acid units, preferably having a molar mass of 20,000 to 25,000 g/mol.

In a further aspect, the present invention refers to the cell culture carrier of polystyrene (TCP) which is coated with a bioactive coating material of the present invention as in one of the above-described variants, wherein the connection of the bioactive coating material is formed via the hydrophobic moieties of the anchor molecules.

The bioactive coating material according to the present invention can be utilized by the producer of the cell culture carrier and also by the end user for coating the cell culture carrier of plastic one-way materials, for example from polystyrene (TCP).

The advantages of the present invention are summarized as follows:

The bioactive coating:
makes a suitably stable anchoring/adhesion on standard cell culture articles possible,
is deposited by a simple adsorption process,
does not generate cytotoxic effects and
stands out as a fully synthetic system through well defined consistent properties.

As compared to the prior art, the present invention shows a markedly improved performance yield, which is realized through a defined consistent quality of the fully synthetic coatings with their bonding strength relative to the plastic surfaces being adjustable, providing for example a cell instructive, especially adhesion mediating functionality of ECM proteins. The combination of different bioactive molecules, in particular, different adhesion ligands, for example, fibronectin and laminin derived peptide sequences permits adjustment to the requirements of different cell cultures and is the basis for a further essential quality advantage relative to the conventional bioactive coatings. The most important advantage resides in the utilization of optimal anchor polymers, which even in complex combinations of biological media remain stably at the plastic surfaces after a simple adsorption from aqueous solution. A most important advantage is also the cost effectiveness. As compared to most of the very costly coatings by the conventional producers, the present invention represents a markedly cost effective alternative, which the end user can deposit on the already existing cost-effective standard cell culture products. The reason is the present price level of the one-way articles. Uncoated one-way cell culture plates are currently priced from € 2.20-3.00 pro plate, while the bioactive coated plates are priced between € 16.00 to 35.00 per plate. The sole synthetic coatings with adhesion peptides covalently coupled to the surface, the CORNING® Synthemax™- coatings are about € 27.00 to 34.00 and are the upper end price point. In addition, adhesion coated surfaces that currently are offered uncoated can be utilized when working with cell culture products.

In providing ready-to-use aqueous solutions for adsorption of bioactive coatings, a marked price advantage can be realized for the end user.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
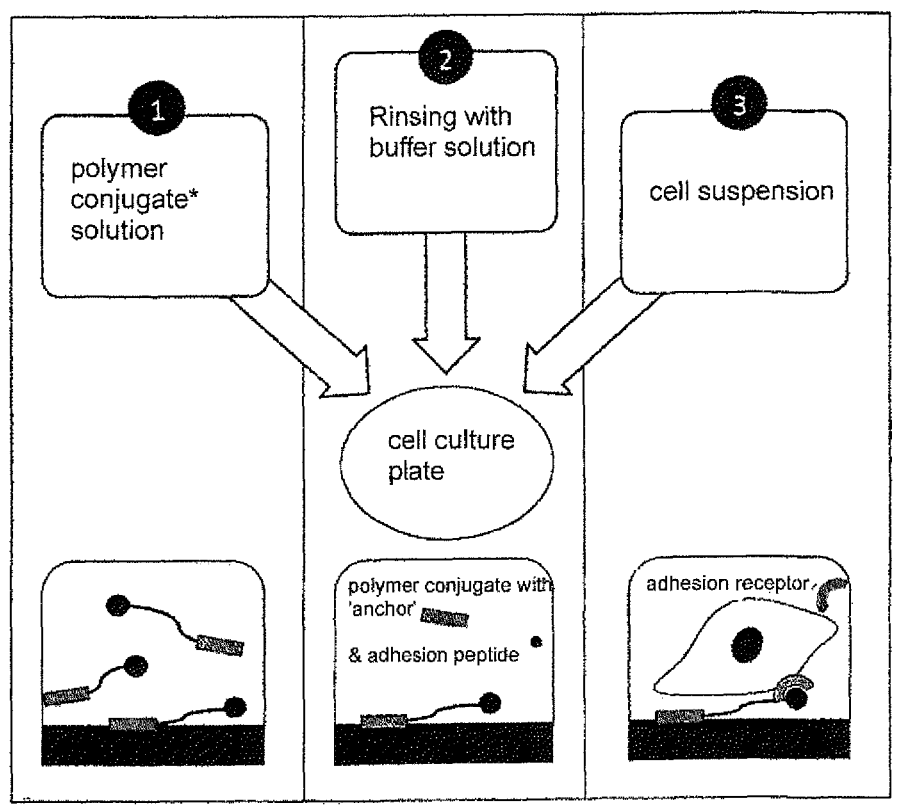
FIG. 1 is a schematic overview of a bioactive cell adhesive coating system.

FIG. 1 shows a schematic overview of a bioactive cell adhesive coating system as an example for a cell-instructive coating system which is suitable for in situ coatings. In step (1) the polymer conjugates are deposited through adsorption from the solution. In step (2) rinsing of the cell culture carriers follows with phosphate buffered sodium chloride solution (PBS) and thus the removal of the not adhered polymer conjugates. In step (3) the culturing of cells on the carrier follows. An essential part of the coating system is the polymer conjugate. Building of these polymer conjugates proceeds stepwise according to known methods. To mediate adhesion, short peptide units derived from ECM proteins that naturally bind cellular receptors are generated through solid phase peptide synthesis. These peptide units are then covalently coupled to the synthetic polymer anchor molecules. The anchor molecules are distinctly interface active and can be effectively deposited on plastic surfaces of various kinds in particular on polystyrene. The deposit of these polymer conjugates can also be realized directly by the end user through adsorption from aqueous solutions, as shown in FIG. 1. Due to the possibility to utilize polymer anchors having differently strong surface affinities which can be coupled with different peptide sequences, the adhesion of different cell types can be defined and cost-effectively modulated for the first time.

The anchor molecule is an amphiphile molecule with a hydrophobic moiety from styrene-, methacrylic acid-, or isobutene units and a hydrophilic moiety of maleic acid anhydride-or maleic acid units. When producing the polymer conjugates, the carboxyl groups of the anchor molecule can be functionalized first in a known manner with maleimide by means of carbodiimide-chemistry. Thereafter, the coupling of the peptide units follows via a Michael-Addition, for example the coupling of RGDP via a cysteine in the sequences, which is build completely from $NH_2$-cysteine/ tryptophane/glycine/arginine/glycine/aspartic acid/serine/ proline-$CONH_2$. The amphiphile anchor molecule polymer 1 consists of alternating copolymer of isobutene and maleic acid anhydride units, wherein the isobutene units form the hydrophobic moiety and the maleic acid anhydride units the hydrophilic moiety. The amphiphilic anchor molecule Polymer 2 consists of a amphiphilic anchor molecule formed from an alternating copolymer from styrene and maleic acid anhydride wherein the styrene units form the hydrophobic moiety and the maleic acid anhydride units the hydrophilic moiety.

Figure 2:
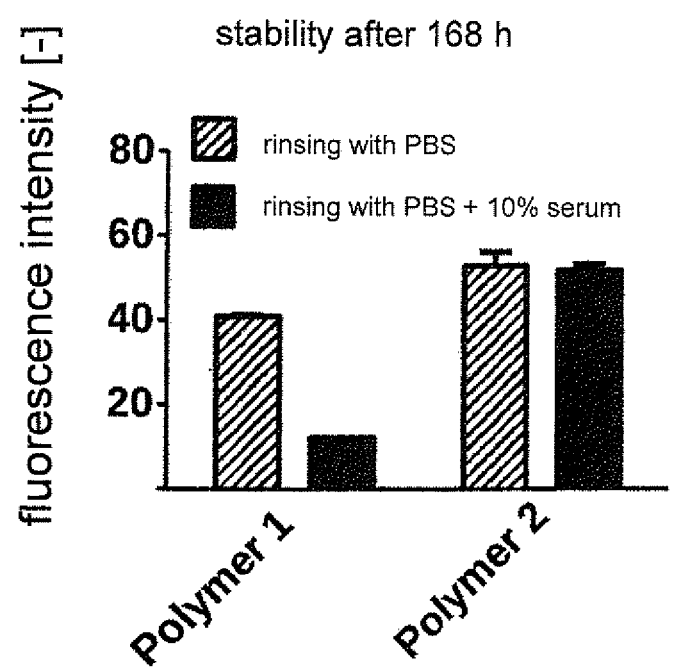
FIG. 2 shows the evaluation of measurements for the layer stability.

FIG. 2 shows the retention of Polymers 1 and 2 at cell culture plastic of polystyrene (TCP) after rinsing with phosphate buffered sodium chloride solution (PBS) and with a mixture of 10% serum dissolved in phosphate buffered sodium chloride solution (PBS) each for 168 hours. To indicate the polymers at the surface, a fluorescence signal is being recorded, wherein the polymers are fluorescently labeled for that purpose.

The Polymer 2 showed a constant surface anchoring upon rinsing with PBS and also when rinsing with a mixture of PBS and 10% serum. Polymer 1 showed a relatively slow desorption when rinsed with PBS, wherein the desorption is stronger when applying the mixture of PBS and 10% serum. Through this slow graded desorption, or depending on the means of rinsing (application relevant cell culture medium) it is possible to establish either a temporally modifiable or a constantly stable anchoring of adhesion ligands.

Figure 3:
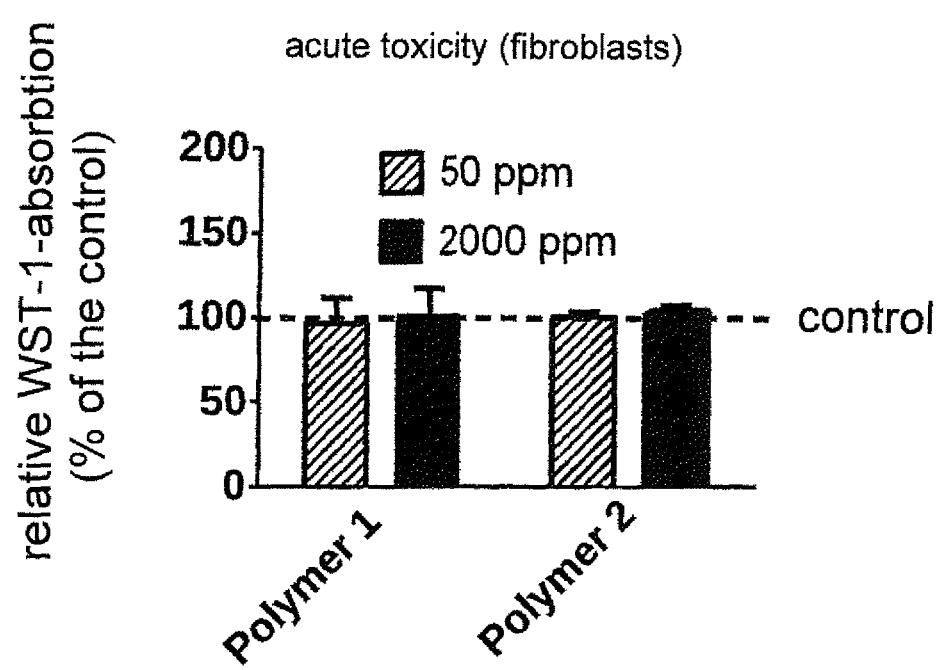
FIG. 3 shows the evaluation of measurements for the polymer toxicity.

FIG. 3 shows the results of a test of acute cell toxicity after pre-adsorption of Polymer 1 and 2 on cell culture plastic made of polystyrene (TCP) by determining the metabolic activity of fibroblasts as compared to the untreated cell culture surface. Determination of cell toxicity is carried out by means of WST-1-Assay, where WST is abbreviated from "water soluble tetrazolium". The WST-1-Assay serves to detect an intact respiration chain in cells. Living cells with an intact mitochondrial succinate-tetrazolium-dehydrogenase-system effect an enzymatic transformation of the lightly red colored tetrazolium salt WST-1 (4-[3-(4-iodophenyl)-2-(4-nitrophenyl)-2H-5(tetrazolio]-1, 3-benzol-disulfonate) into the dark red formazan. This color change can be photometrically measured and analyzed in a spectral photometer. In FIG. 3 the spectral photometric WST absorption is shown as a relative value after pre-absorption of polymer 1 and 2 each as compared to the absorption in the presence of an untreated cell culture surface which corresponds to a value of 100%.

As seen in FIG. 3, neither Polymer 1 nor Polymer 2, in an absorbed state show a toxic effect at a dosage relevant for the application of 50 respectively, 2000 ppm.

Figure 4:
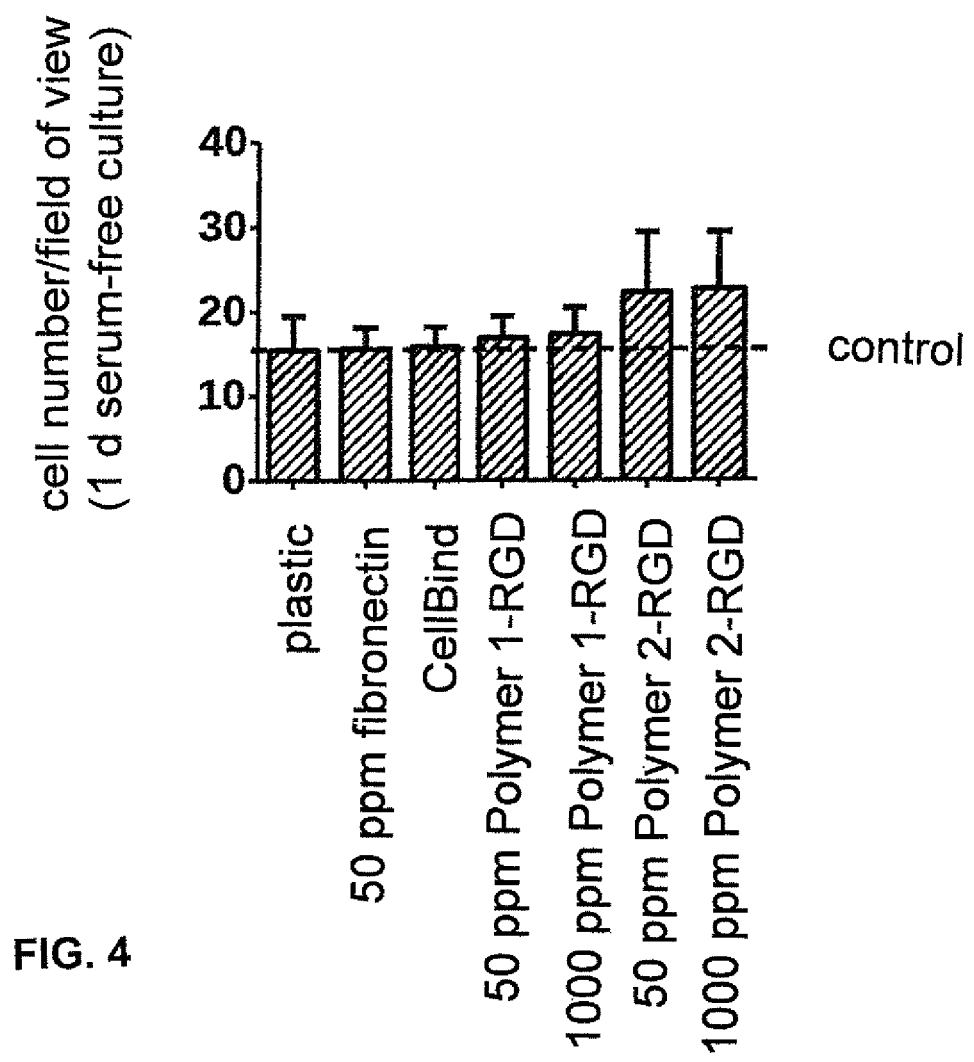
FIG. 4 shows the analysis of initial cell adhesion through determination of the number of adhering cells at various modified surfaces.

FIG. 4 shows the results of the analysis of the cell adhesion of human endothelial cells (HUVEC) at the with Polymers 1 and 2 conjugated with RGD (Polymer 1-RGD and Polymer 2-RGD) via pre-adsorption, modified surfaces by means of counting. The investigation of potentially adhesion mediating effects of the Polymers conjugated with RGD. The experimental investigations are carried out after a 24-hour serum-free culture.

For the negative control a plastic cell culture carrier was used. For the positive control fibronectin was used which was pre-adsorbed from a solution with a concentration of 50 ppm. A further comparative analysis was carried out on a cell culture carrier of plasma treated plastic (Corning® CellBIND®). A portion of the investigation was done each with 50 ppm or 1000 ppm conjugate of Polymer 1 and RGD respectively on a cell culture carrier surface pre-prepared through adsorption. Another part of the investigation was carried out with each 50 ppm or 1000 ppm conjugate of Polymer 2 and RGD respectively on a cell culture carrier surface pre-prepared through adsorption.

In serum-free culture the presence of Polymers 1 and 2 (Polymer 1-RGD and Polymer 2-RGD) raises the number of adhering cells, wherein this increase is much more amplified when applying conjugate of adhesion ligand and Polymer 2 (Polymer 2-RGD) as compared to applying conjugate of adhesion ligand and Polymer 1 (Polymer 1-RGD).

Figure 5:
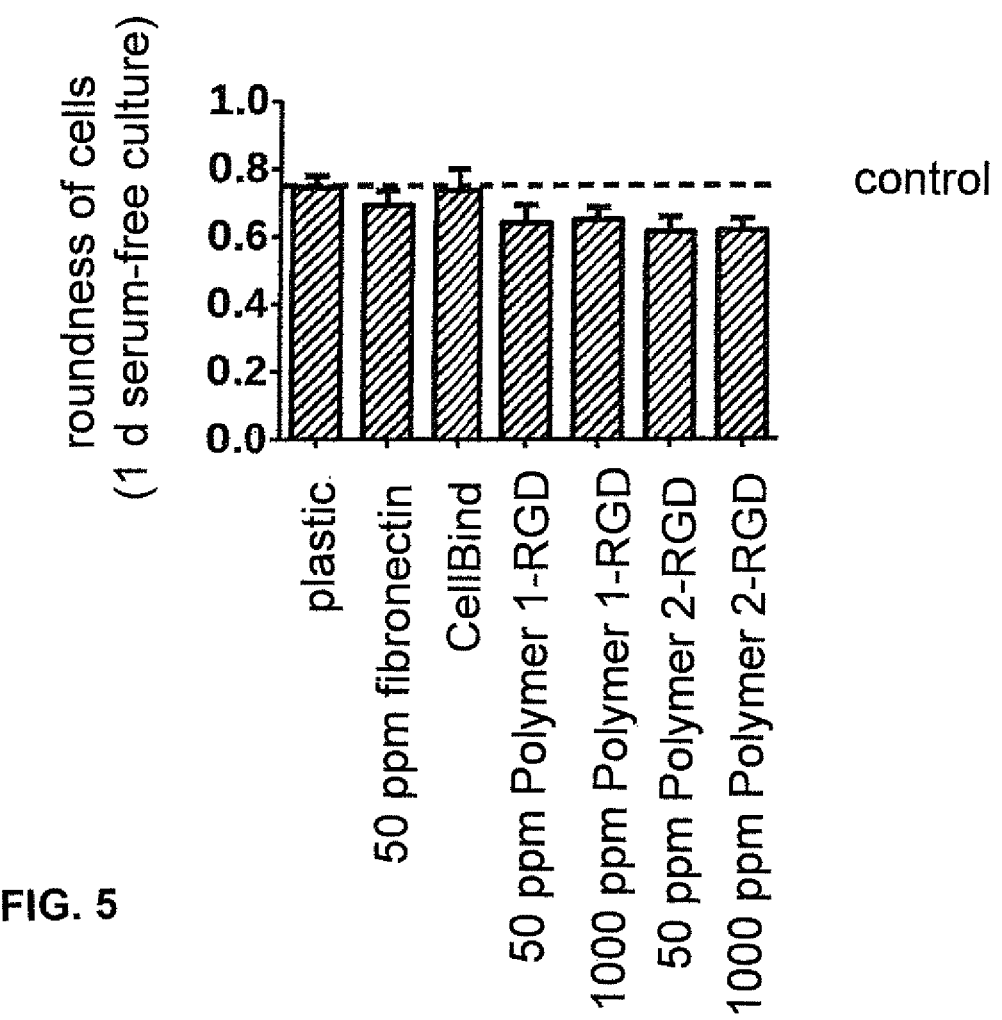
FIG. 5 shows the analysis of initial cell adhesion through determination of cell elongation at the various modified surfaces.

FIG. 5 shows the morphology, described as aspect ratio, of human endothelial cells after pre-adsorption of the conjugates of adhesion ligand and the two Polymers 1 and 2 (Polymer 1-RGD and Polymer 2-RGD) on the cell culture plastic of polystyrene (TCP). The biologically desirable elongation of the endothelial cells is expressed by a low aspect ratio. This is the ratio of the short to the long axis, the co-efficient 1 corresponds to a round cell, a co-efficient<1 corresponds to the desired elongated morphology. The measurements were carried out each after 24 hours of serum-free culture.

In serum-free culture the presence of the Polymers 1 and 2 conjugated with RGD (Polymer 1-RGD and Polymer 2-RGD) raises the elongation of adherent cells even more effectively than in the positive control with fibronectin. This means that with both conjugates, higher elongation values are realized as compared with the comparative probes on plastic, with 50 ppm fibronectin and with the cell culture carrier from plasma treated plastic CellBind. Thus, for the conjugate of adhesion ligand with Polymer 2 (Polymer 2-RGD) even lower roundness values were measured than for the conjugate of adhesion ligand Polymer 1 (Polymer 1-RGD). The roundness values which were measured for the different dosages of 50 ppm respectively 1000, did not differ substantially.

What is claimed is:

1. A method of coating a plastic cell culture carrier, comprising:
   coating the cell culture carrier with a bioactive coating material, the bioactive coating material provided in an aqueous solution, wherein the bioactive coating material comprises a polymer conjugate, said polymer conjugate obtained or obtainable from linking an amphiphilic polymer anchor molecule and one or more biologically active molecules,
   wherein the polymer anchor molecule is an alternating copolymer with alternating isobutene and maleic acid units or alternating styrene and maleic acid units, and
   wherein the bioactive coating material is adsorbed from the aqueous solution to the carrier via the styrene or isobutene units of the polymer anchor molecule.

2. The method of claim 1, further comprising a step of rinsing the coated cell culture carrier to remove non-adhered polymer conjugates.

3. The method of claim 2, wherein the rinsing step is carried out with phosphate buffered sodium chloride solution.

4. The method of claim 1, wherein the one or more biologically active molecules are coupled to the amphiphilic polymer anchor molecule via an enzymatically cleavable peptide.

5. The method of claim 4, wherein the enzymatically cleavable peptide is cleavable by metaloproteases or cysteine-, aspartyl-, serine-or threonyl-proteases.

6. The method of claim 4, wherein the enzymatically cleavable peptide consists of 5 to 25 amino acid moieties.

7. The method of claim 4, wherein the cleavable peptide comprises or consists of a peptide of the amino acid sequence SEQ ID NO. 1.

8. The method of claim 1, wherein the biologically active molecule is a signal molecule.

9. The method of claim 8, wherein the signal molecule is selected from the group consisting of neurotransmitters, hormones, cytokines, growth factors and chemokines.

10. The method of claim 1, wherein the biologically active molecule is a peptide with 3 to 50 amino acid moieties.

11. The method of claim 1, wherein the biologically active molecule is an adhesion peptide with 3 to 50 amino acid moieties.

12. The method of claim 10, wherein the biologically active molecule is a peptide that is derived from a protein of the extracellular matrix.

13. The method of claim 10, wherein the biologically active molecule is a peptide derived from collagen, fibronectin or laminin.

14. The method of claim 11, wherein the adhesion peptide comprises one or more amino acid sequences selected from the group consisting of RGD, SEQ ID NO. 2, SEQ ID NO. 3, SEQ ID NO. 4, SEQ ID NO. 5, SEQ ID NO. 6 and SEQ ID NO. 7.

15. The method of claim 1, wherein the polymer anchor molecule is a molecule of a copolymer with alternating isobutene and maleic acid units.

16. The method of claim 15, wherein the polymer anchor molecule has a molar mass of 4,000 g/mol.

17. The method of claim 1, wherein the polymer anchor molecule is a copolymer with alternating styrene-and maleic acid units.

18. The method of claim 17, wherein the polymer anchor molecule has a molar mass of 20,000 to 25,000 g/mol.

* * * * *